United States Patent [19]

Huprich

[11] Patent Number: 5,413,780
[45] Date of Patent: May 9, 1995

[54] LIQUID SKIN COATING OR PROTECTANT

[76] Inventor: Carl A. Huprich, 22333 County Rd. 62 N., Robertsdale, Ala. 36567

[21] Appl. No.: 142,007

[22] Filed: Oct. 28, 1993

[51] Int. Cl.$^6$ ...................... A61K 9/10; A61K 31/125
[52] U.S. Cl. ............................ 424/78.02; 424/78.03; 424/78.04; 424/78.05; 424/401
[58] Field of Search ................. 424/401, 78.05, 78.02, 424/78.03, 78.04, 78.06, 78.07

[56] References Cited

U.S. PATENT DOCUMENTS

| | | | |
|---|---|---|---|
| 2,824,559 | 2/1958 | Sullivan | 128/157 |
| 4,496,322 | 1/1985 | Sandham et al. | 433/217 |
| 4,880,416 | 11/1989 | Horiuchi et al. | 604/307 |
| 4,913,897 | 4/1990 | Chvapil et al. | 424/59 |
| 5,013,769 | 5/1991 | Murray et al. | 523/111 |

OTHER PUBLICATIONS

Japan Abstract of JP 57-109706 Torbibona et al Jul. 1982.
Japan Abstract of JP-02-85207 Tanaka et al Jul. 1988.

*Primary Examiner*—Thurman K. Page
*Assistant Examiner*—Peter F. Kulkosky

[57] ABSTRACT

A method of increasing slip or reducing coefficient of friction to protective coatings for skin to reduce damage to exposed skin tissue is provided by adding inert powder with low coefficient of friction to tincture or solution suitable for skin application. Tincture of benzoin and polyethylene powder comprise a rapidly drying coating or protectant composition with the above skin adhesive properties.

1 Claim, No Drawings

LIQUID SKIN COATING OR PROTECTANT

BACKGROUND OF THE INVENTION

This invention generally relates to a liquid composition that may be applied to animal or human skin, that dries rapidly, and provides protection from abrasion, irritation, and sores, through a layer of adhering material with reduced coefficient of friction.

Liquids, lotions, creams, and pastes that remain wet or dry and form a film are well known in the industry. Examples include tincture of benzoin (gum), collodion, modified ethyl acetate, cellulose nitrate, and pyroxylin in solutions. Some trade names include "Skin Shield" and "Nu-Skin". In addition, Sullivan, in U.S. Pat. No. 2,824,559, described a plastic cot or bandage for covering and protecting hands and other parts of the body, including wounds. Firth, et al, in U.S. Pat. No. 3,682,559, described a method for treating and repairing wounds of animals by applying urethane resin to hoof surfaces. Dell, et al, in U.S. Pat. No. 4,584,192, described a film forming composition for protecting wounds and releasing anti-microbial agents to the skin. Webster, in U.S. Pat. No. 4,664,662, described an absorbent wound dressing suitable for use in deep and cavernous wounds. Horichi, et al, in U.S. Pat. No. 4,880,416, described a dermal bandage comprising a film like adhesive for protecting wounds. Gould, in U.S. Pat. No. 4,156,067, described a polyurethane polymer which could be used in drug delivery systems or as burn dressings.

Each of these materials and patents provide skin protection from external contamination, some with added medicinal properties, but all have high coefficients of friction that increase the likelihood of abrasion or irritation of the skin surface.

SUMMARY OF INVENTION

This invention provides a liquid or gel like material that may be applied to skin surfaces, that dries rapidly to form a barrier to external contamination while reducing the coefficient of friction with other surfaces or materials. This reduces the abrasion and irritation of the skin area that might cause sores, galling, blisters, or raw spots.

DESCRIPTION OF THE PREFERRED EMBODIMENT

Adding an inert powder that provides slip in a dry form to an excellent adhesive skin binder in solvent provides desired properties to an established skin protectant. Specifically, we have mixed plastic (Polyethylene) powder to tincture of benzoin, gum, or solution, to accomplish the desired results. Tincture of benzoin has been used extensively to protect skin areas and increase adhesion of other materials to the skin surface. High friction reduces the overall value of this material. Benzoin gum does adhere well to skin and acts as an effective binder for the plastic powder that reduces friction and increases slip on the exposed face. Other materials may be combined to perform likewise.

What is claimed is:

1. A liquid, rapidly drying coating or protectant composition comprising tincture of benzoin and polyethylene powder, said composition having improved slip or reduced coefficient of friction in dry form.

* * * * *